(12) United States Patent
Ma et al.

(10) Patent No.: US 8,544,711 B2
(45) Date of Patent: *Oct. 1, 2013

(54) SURGICAL STAPLER WITH TACTILE FEEDBACK SYSTEM

(75) Inventors: Yong Ma, Cheshire, CT (US); Russell S. Heinrich, Madison, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/493,061

(22) Filed: Jun. 11, 2012

(65) Prior Publication Data

US 2012/0255985 A1 Oct. 11, 2012

Related U.S. Application Data

(63) Continuation of application No. 12/793,300, filed on Jun. 3, 2010, now Pat. No. 8,205,779.

(60) Provisional application No. 61/227,823, filed on Jul. 23, 2009.

(51) Int. Cl.
*B21J 15/28* (2006.01)
*B27F 7/17* (2006.01)
*A61B 17/04* (2006.01)
*A61B 17/10* (2006.01)

(52) U.S. Cl.
USPC ................................................. 227/175.3

(58) Field of Classification Search
USPC ............... 227/1–8, 175.1–182.1; 294/119.3; 29/270, 278; 269/3, 6, 95; 606/75, 138, 606/192, 201–236
See application file for complete search history.

(56) References Cited

U.S. PATENT DOCUMENTS

| 1,937,294 | A |   | 11/1933 | Post |
| 2,466,042 | A |   | 4/1949 | Reich et al. |
| 3,802,249 | A | * | 4/1974 | Clawson .......................... 374/2 |
| 4,534,208 | A |   | 8/1985 | Macin et al. |
| 4,606,328 | A |   | 8/1986 | Thoman |
| 4,863,088 | A |   | 9/1989 | Redmond et al. |
| 4,883,462 | A | * | 11/1989 | Williamson et al. .......... 604/540 |
| 5,118,907 | A | * | 6/1992 | Stout et al. .................... 174/135 |
| 5,258,007 | A |   | 11/1993 | Spetzler et al. |
| 5,303,851 | A |   | 4/1994 | Libit et al. |
| 5,422,272 | A | * | 6/1995 | Papp et al. ................. 435/285.2 |
| 5,464,144 | A |   | 11/1995 | Guy et al. |

(Continued)

FOREIGN PATENT DOCUMENTS

| EP | 1769756 | 4/2007 |
| EP | 1813201 | 8/2007 |

(Continued)

OTHER PUBLICATIONS

European Search Report corresponding to European Application No. EP 10 25 1415.5, mailed Jun. 10, 2010 and completed on Sep. 22, 2010; 3 pages.

*Primary Examiner* — Robert Long

(57) ABSTRACT

A surgical instrument comprising a handle portion, an elongated body portion extending distally from the handle portion, and a tool adjacent the distal portion of the elongated body portion and having at least one jaw movable to a clamping position to clamp tissue. A tactile feedback system includes an expandable member extending from the handle portion, the expandable member providing a tactile indicator of a tissue parameter of tissue clamped by the least one jaw.

19 Claims, 4 Drawing Sheets

(56) References Cited

U.S. PATENT DOCUMENTS

| | | | |
|---|---|---|---|
| 5,497,934 A | 3/1996 | Brady et al. | |
| 5,503,320 A | 4/1996 | Webster et al. | |
| 5,518,163 A | 5/1996 | Hooven | |
| 5,518,164 A | 5/1996 | Hooven | |
| 5,571,153 A | 11/1996 | Wallsten | |
| 5,685,474 A | 11/1997 | Seeber | |
| 5,762,256 A | 6/1998 | Mastri et al. | |
| 5,762,609 A * | 6/1998 | Benaron et al. | 600/473 |
| 5,771,490 A | 6/1998 | Reynolds et al. | |
| 5,772,597 A * | 6/1998 | Goldberger et al. | 600/473 |
| 5,800,493 A | 9/1998 | Stevens et al. | |
| 5,843,483 A | 12/1998 | Theriault et al. | |
| 5,987,705 A | 11/1999 | Reynolds | |
| 6,066,132 A | 5/2000 | Chen et al. | |
| 6,139,571 A | 10/2000 | Fuller et al. | |
| 6,217,585 B1 * | 4/2001 | Houser et al. | 606/108 |
| 6,224,548 B1 | 5/2001 | Gopinathan et al. | |
| 6,396,224 B1 * | 5/2002 | Luff et al. | 318/16 |
| 6,585,173 B2 | 7/2003 | Schmon et al. | |
| 6,651,486 B1 | 11/2003 | Johnson et al. | |
| 6,834,647 B2 | 12/2004 | Blair et al. | |
| 6,879,880 B2 | 4/2005 | Nowlin et al. | |
| 6,945,981 B2 * | 9/2005 | Donofrio et al. | 606/169 |
| 6,969,384 B2 | 11/2005 | de Juan et al. | |
| 7,021,180 B2 * | 4/2006 | Crane | 81/467 |
| 7,083,613 B2 | 8/2006 | Treat | |
| 7,137,954 B2 * | 11/2006 | Thede et al. | 600/500 |
| 7,183,764 B2 * | 2/2007 | Goldfine et al. | 324/238 |
| 7,464,847 B2 | 12/2008 | Viola et al. | |
| 7,624,902 B2 | 12/2009 | Marczyk et al. | |
| 7,669,598 B2 | 3/2010 | Rick et al. | |
| 8,118,206 B2 * | 2/2012 | Zand et al. | 227/175.1 |
| 8,205,779 B2 * | 6/2012 | Ma et al. | 227/175.2 |
| 2003/0029451 A1 | 2/2003 | Blair et al. | |
| 2003/0129382 A1 | 7/2003 | Treat | |
| 2004/0082859 A1 * | 4/2004 | Schaer | 600/459 |
| 2005/0066969 A1 * | 3/2005 | Rick et al. | 128/204.18 |
| 2005/0124945 A1 * | 6/2005 | Powers et al. | 604/310 |
| 2005/0234428 A1 * | 10/2005 | Spohn et al. | 604/533 |
| 2005/0245910 A1 * | 11/2005 | Wright et al. | 606/1 |
| 2006/0173486 A1 * | 8/2006 | Burke et al. | 606/193 |
| 2006/0200028 A1 * | 9/2006 | Evans | 600/485 |
| 2006/0271094 A1 | 11/2006 | Hudson et al. | |
| 2006/0273135 A1 * | 12/2006 | Beetel | 227/175.1 |
| 2006/0278680 A1 * | 12/2006 | Viola et al. | 227/176.1 |
| 2007/0078484 A1 | 4/2007 | Talarico et al. | |
| 2007/0179408 A1 | 8/2007 | Soltz | |
| 2007/0208330 A1 * | 9/2007 | Treat et al. | 606/30 |
| 2008/0009925 A1 * | 1/2008 | Abboud et al. | 607/101 |
| 2008/0139876 A1 | 6/2008 | Kim | |
| 2008/0234788 A1 | 9/2008 | Wasowski | |
| 2008/0245867 A1 | 10/2008 | Mynhardt | |
| 2008/0267599 A1 | 10/2008 | Arnold et al. | |
| 2009/0076534 A1 | 3/2009 | Shelton, IV | |
| 2009/0088735 A1 * | 4/2009 | Abboud et al. | 606/22 |
| 2009/0234273 A1 | 9/2009 | Intoccia et al. | |
| 2009/0314820 A1 | 12/2009 | Green et al. | |
| 2010/0057105 A1 | 3/2010 | Sorrentino et al. | |
| 2010/0114089 A1 | 5/2010 | Truckai et al. | |
| 2010/0137882 A1 | 6/2010 | Quaid, III | |
| 2010/0249615 A1 | 9/2010 | Kukita et al. | |
| 2010/0270394 A1 | 10/2010 | Kwon | |
| 2011/0230880 A1 * | 9/2011 | Chojin et al. | 606/45 |
| 2011/0271504 A1 | 11/2011 | Preti | |

FOREIGN PATENT DOCUMENTS

| | | |
|---|---|---|
| EP | 1813206 | 9/2007 |
| EP | 1997438 | 12/2008 |
| WO | WO-98/30153 | 7/1998 |

* cited by examiner

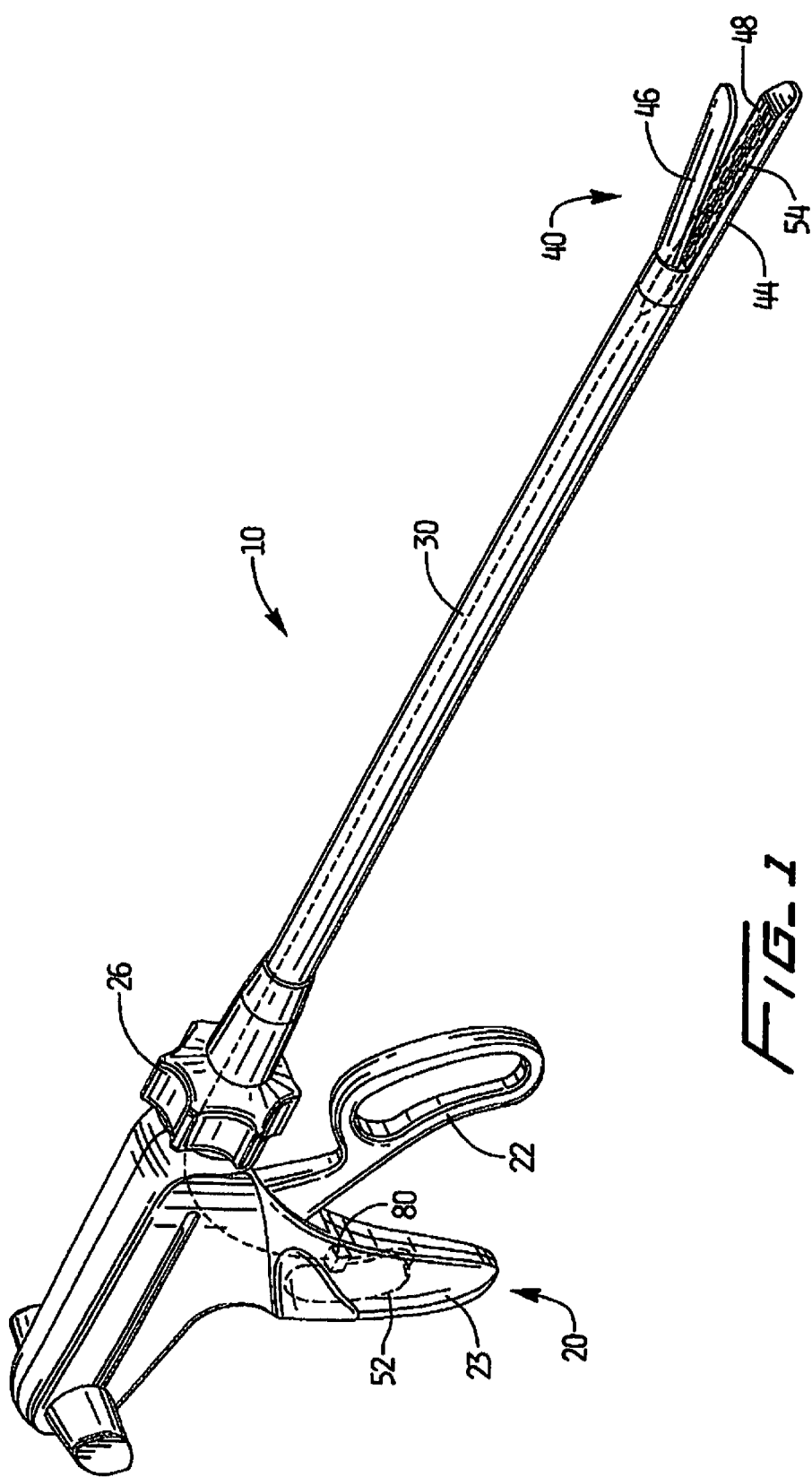

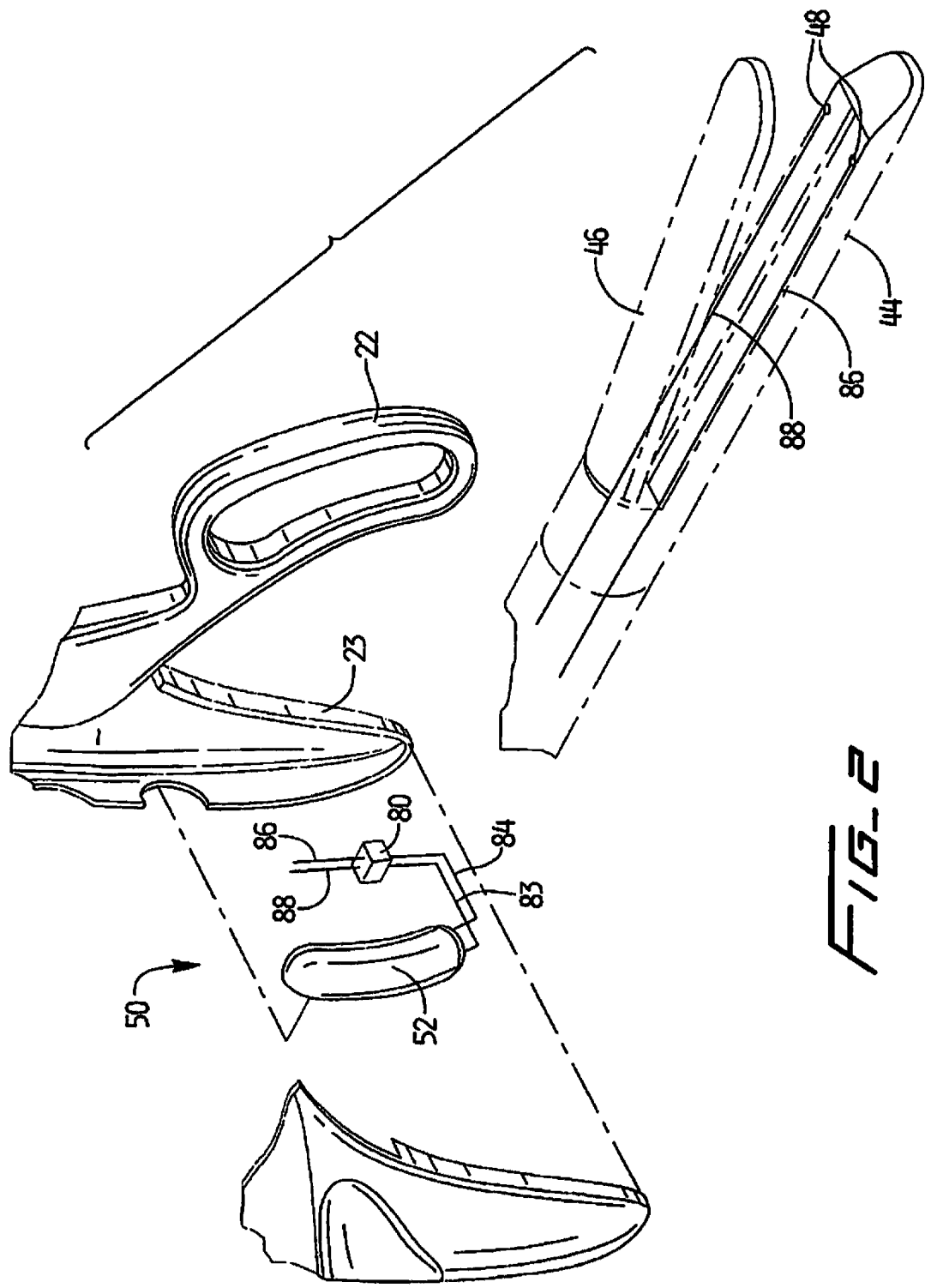

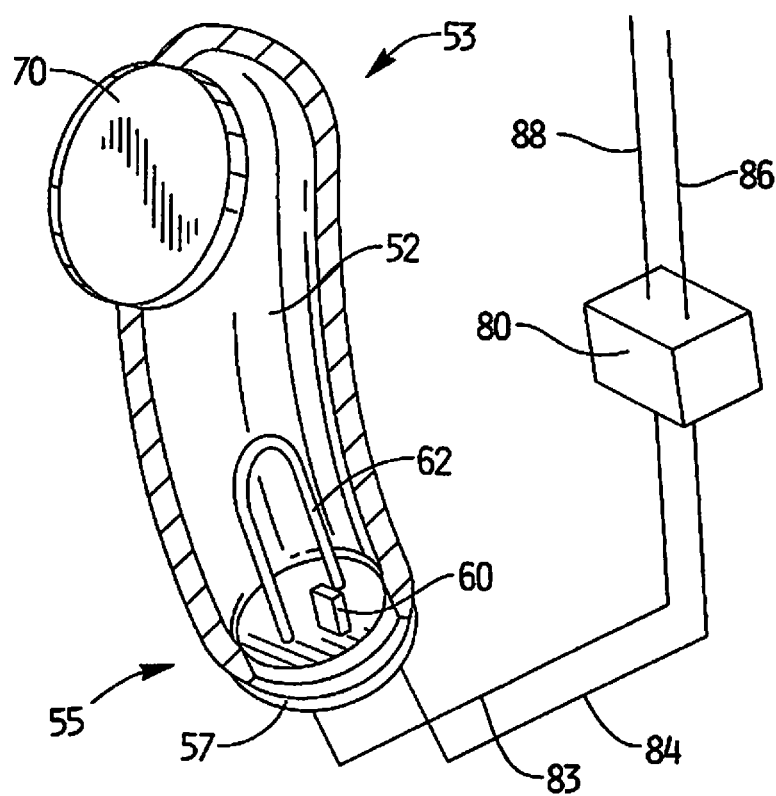
FIG_3

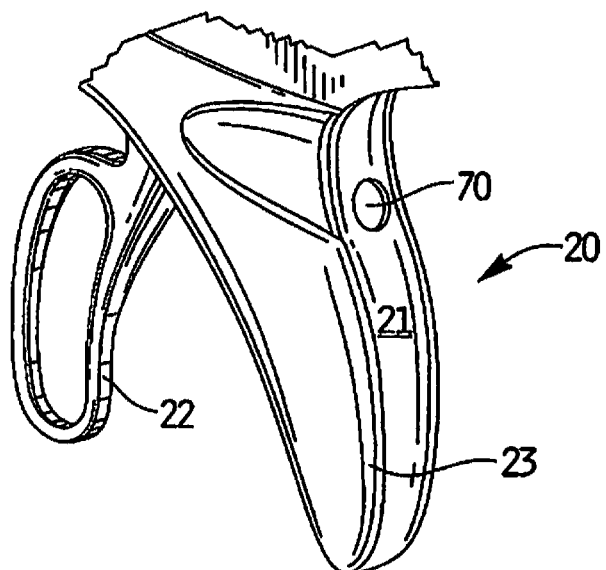
FIG_4
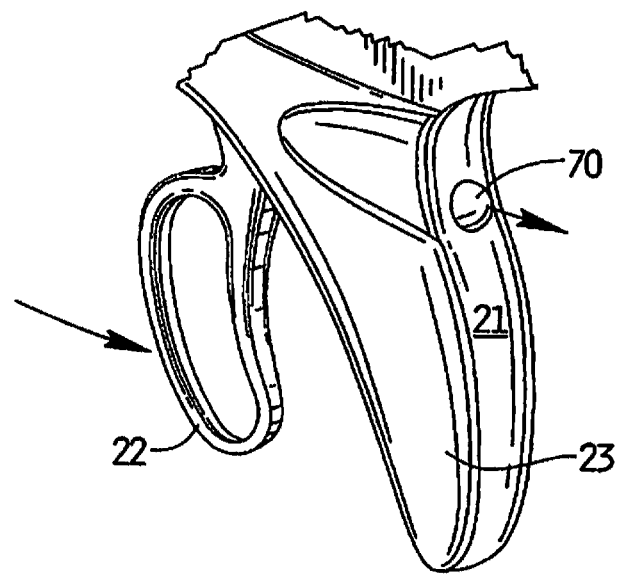
FIG_5

SURGICAL STAPLER WITH TACTILE FEEDBACK SYSTEM

This application is a continuation of patent application Ser. No. 12/793,300, filed on Jun. 3, 2010 now U.S. Pat. No. 8,205,779, which claims priority to provisional application Ser. No. 61/227,823, filed Jul. 23, 2009. The entire contents of each of these applications are incorporated herein by reference.

BACKGROUND

1. Technical Field

The present disclosure relates to a surgical stapler, and more particularly, to a surgical stapler having a tactile feedback system.

2. Background of Related Art

A variety of different types of surgical instruments have been developed for manipulating, identifying, treating, repairing and/or excising tissue including organs or portions thereof located within body cavities for performing minimally invasive procedures. In such procedures, a surgical stapler is inserted through an incision, cannula, or natural orifice to a surgical site where a surgical procedure is to take place.

One type of surgical stapler often utilized in laparoscopic procedures is an endoscopic stapling instrument having a pair of jaws, one of which is pivotable with respect to the other to clamp tissue therebetween. After clamping of the tissue, the firing trigger is actuated to apply rows of staples to the tissue. Examples of such instruments are disclosed for example in U.S. Pat. Nos. 5,762,256 and 5,865,361. Optionally, a knife is actuated with the staple firing to sever tissue between the rows of staples. During open surgical procedures, the surgeon cannot only visualize the tissue but can feel the tissue with his or her fingers and assess the pressure/clamping of the tissue. With endoscopic staplers, the jaws are positioned in the body cavity and the handle gripped by the user is outside the body. Although the surgeon can view the tissue on the video monitor, the surgeon does not have access with his or her fingers to the clamped tissue within the body cavity.

Therefore, in the absence of direct manual access, it would be advantageous to provide an endoscopic/laparoscopic stapling instrument that enhances the surgeon's ability to "sense" the tissue.

SUMMARY

The present application advantageously provides an electronically actuated tactile feedback indicator system. In accordance with one aspect of the present disclosure, a surgical instrument is provided comprising a handle portion, an elongated body portion adjacent the handle portion, and a tool assembly adjacent a distal portion of the elongated body portion and having at least one jaw movable to a clamping position to clamp tissue. A tactile feedback system includes an expandable member extending from the handle portion, the expandable member providing a tactile indicator of a tissue parameter of tissue clamped by the least one jaw.

In preferred embodiments the tissue parameter can be a force or a pressure applied by the at least one jaw to the tissue.

In a preferred embodiment, the tactile feedback system includes an air chamber having a heating element therein to change the temperature within the chamber, and the expandable member is in fluid communication with the air chamber such that an increase in temperature of the heating element increases the air pressure in the chamber to cause expansion of the expandable member. The system preferably further includes a controller and a sensor positioned adjacent the tool assembly to provide an electrical signal to the controller of a measured tissue parameter, the controller providing an electrical signal to the heating element in response to the measured tissue parameter. A thermistor may also be provided. Alternatively, other sensors can be provided to measure for example air pressure within the chamber or to measure balloon parameters such as strain, force and/or displacement.

In a preferred embodiment, the expandable member is positioned on a rear surface of the handle assembly.

The present disclosure provides in another aspect a surgical fastener applying instrument comprising a handle portion including a firing lever, an elongated body portion extending distally from the handle portion, a tool assembly adjacent a distal portion of the elongated body portion having at least one jaw movable to a clamping position to clamp tissue and a plurality of surgical fasteners. A sensor is positioned adjacent the tool assembly. A firing mechanism fires the fasteners from the tool assembly into body tissue upon actuation of a firing lever. A tactile feedback system responsive to the sensor includes an expandable member extending from the handle portion, the expandable member providing a tactile indication of one of a pressure or force on tissue clamped by the least one jaw.

In a preferred embodiment, the expandable member expands in response to heating of a heater element positioned within an air chamber of the feedback system to change the air pressure within the chamber. In a preferred embodiment, the feedback system includes a controller positioned within the handle assembly and outside the air chamber to convert input signals of pressure or force on tissue from the sensor to output temperature signals to the heater element.

BRIEF DESCRIPTION OF THE DRAWINGS

Various embodiments of the presently disclosed device are described herein with reference to the drawings, wherein:

FIG. 1 is a perspective view of one type of surgical instrument having a tactile feedback indicator system of the present disclosure;

FIG. 2 is an exploded view of a portion of the handle assembly of the instrument of FIG. 1 and a perspective view of the jaws of the instrument of FIG. 1 having sensors in electrical communication with the indicator;

FIG. 3 is an enlarged view of the tactile feedback system of the present disclosure in partial cross section;

FIG. 4 is a rear perspective view of the handle assembly of FIG. 1 with the expandable element of the tactile feedback system in the non-expanded condition; and FIG. 5 is a rear perspective view of the handle assembly of FIG. 1 with the expandable element of the tactile feedback system in the expanded condition.

DETAILED DESCRIPTION

In the present disclosure, it is envisioned that the tactile feedback indicator system disclosed herein may be utilized with any endoscopic or remotely actuated surgical device having a tool assembly which is suitable for insertion into a body cavity (e.g., circular anastomosis staplers, linear staplers, transverse staplers, clip appliers, fastener applying instruments and the like). It is also envisioned that the embodiments of the present disclosure may be utilized to access various surgical sites via natural orifice openings, or incisions created by surgeons (e.g., mouth, anus, percutaneous incisions, etc.). For purposes of explaining the present disclosure, by way of example, an endoscopic linear stapler will be the exemplary surgical instrument.

In the drawings and in the description which follows, the term "proximal", as is traditional, will refer to the end of the surgical device or instrument of the present disclosure which is closer to the operator, while the term "distal" will refer to the end of the device or instrument which is further from the operator.

Referring initially to FIG. 1, a surgical instrument is provided which is illustrated as a surgical stapling device 10 having a handle assembly 20, an elongated endoscopic portion 30 and a tool assembly 40 including a cartridge assembly 44. Handle assembly 20 includes an approximation firing handle 22 for approximating the tool assembly 40 and firing the staples from cartridge assembly 44. Handle 22 moves relative to stationary grip 23. The staples are advanced into contact with anvil pockets on anvil 46 of tool assembly 40. In the illustrated embodiment, anvil member 46 pivots with respect to cartridge assembly 44 to clamp tissue therebetween. Details of the operation of the endoscopic instrument are disclosed in U.S. Pat. Nos. 5,762,256 and 5,865,361, the entire contents of which are incorporated herein by reference. A rotation knob 26 rotates the endoscopic portion 30 and tool assembly 40 about the longitudinal axis of endoscopic portion 30.

Cartridge assembly 44 includes a linear array of staple pockets 54. Each staple pocket 54 houses a staple (not shown). Several parallel rows of staples can be provided. A knife can optionally be provided to cut the tissue between the rows of staples.

Referring to FIGS. 2 and 3, a preferred embodiment of the tactile feedback indicator system will now be described. The indicator system, which provides tactile feedback to the instrument user, is designated generally by reference numeral 50, and is positioned in the handle assembly 20. The system 50 preferably includes a chamber 52, a heating element 62, a thermistor 60, an expandable member 70 and a controller 80. The heating element 62 is positioned within the chamber 52 to raise the temperature within the chamber 52 as discussed in more detail below. The expandable member 70, which can be in the form of a balloon, is illustratively positioned at a first end portion 53 of the chamber and in fluid communication with the chamber 52. Other positions are also contemplated. As shown, the expandable member 70 extends transversely from the chamber 52 for access to the user described below. At the second opposing end portion 55 of chamber 52, a cap 57 or other sealing member seals the end of the chamber 52 to entrap air inside. When the temperature within the air chamber 52 increases, the air pressure within the chamber 52 increases to cause inflation of the expandable member 70 as described in more detail below.

The thermistor 60 performs a dual function. The thermistor 60 which measures the temperature in the air chamber 52 provides for cutoff of current by the controller 80 if the temperature in the air chamber 52 exceeds a predetermined value. This prevents overheating and possible damage to the system or device components. The thermistor 60 also provides a feedback function to maintain a proportional heating element temperature in response to a tissue parameter as described in more detail below.

An electronic controller 80 is positioned outside the chamber 52 and in electrical communication via wires 83, 84 with the heating element 62 and the thermistor 60, respectively. Preferably, the controller 80 is positioned within the handle assembly 20 and in a preferred embodiment in the stationary grip 23. The controller 80 is also in electrical communication with the sensors 48 positioned on the tool assembly 40 via conduits, e.g. wires, 86, 88. The sensors 48 in the preferred embodiments sense pressure or force of the jaws on tissue and transmit this information to the controller 80 via conduits, e.g. wires, 86, 88. The sensors 48 are shown by way of example on opposing sides of the staple line of the cartridge assembly, it being understood that alternatively a different number of sensors can be utilized and can be placed on other regions of the tool assembly 40, e.g. at the proximal region of the cartridge assembly, closer to the staple line, etc. The sensors can also be utilized to sense other tissue parameters or sense instrument jaw parameters such as the degree of jaw closure.

The controller 80 is programmed to process input tissue parameters and output temperature parameters. That is, in the embodiment sensing tissue pressure, controller 80 converts the input electrical signals of the measured tissue pressure from sensors 48 to temperature output electrical signals transmitted to the heating element 62. More specifically, for a given tissue pressure, a desired temperature is preset. This temperature is preselected to correspond to a desired increase in air pressure in chamber 52. The amount of increase in air pressure is preselected to correspond to the amount of expansion of the expandable element 70. Consequently, as the pressure on tissue is increased, the temperature of the heating element 62 will increase to a preset degree, predetermined and programmed within the controller. For example, assume for a pressure reading P1 the temperature objective is T1 in order to achieve a proportional expansion of the expandable element 70 to a size E1. If the pressure increases to P2, then the proportional preset temperature objective is at a higher temperature T2. As the temperature increases from T1 to T2, the amount which the expandable member 70 expands will increase to E2 due to the increased pressure within the air chamber 52. Thus, the greater the pressure on tissue, the greater the temperature of the heating element and the greater the expansion (i.e. size) of the member 70 due to the increased pressure in air chamber 52. Conversely, less tissue pressure translates to a lower temperature and less expansion due to the lower pressure in air chamber 52. To summarize:

↑Tissue Pressure→↑Temperature→↑Air chamber pressure→↑Balloon expansion and conversely, ↓Tissue Pressure→↓Temperature→↓Air chamber pressure→↓Balloon expansion The temperature values are preset in accordance with pressure readings, force readings or other desired tissue parameters. In a preferred embodiment, the temperature value would change in proportion to the change in the tissue pressure. In this manner, a more sensitive tactile feel could be provided. This relationship can apply to different measured tissue parameters as well.

It is also contemplated that preset ranges could be provided. In this manner, a tissue parameter range would provide an expansion of the expandable member to a predetermined size; another range would provide expansion to another predetermined size, etc. It is also contemplated that instead of various expanded positions, the system can be configured so expandable element has a non-expanded (non-inflated) position and an expanded (inflated) position once the sensed tissue parameter, e.g. tissue pressure, exceeds a threshold value.

Thermistor 60 functions to monitor the temperature of the air in the chamber 52. As the heating element 62 is heated to increase the air temperature, the output of the thermistor 60 will change accordingly. The controller continuously monitors the output value of the thermistor 60. If the temperature measurement of the thermistor 60 exceeds a maximum predetermined value, the controller 80 will cut off current flow to the heating element 62, thereby ensuring the heating element 62 does not overheat and the system remains safe. Further, if the air in chamber 52 does not reach a temperature value corresponding to the output temperature as determined by the tissue data, the measurement of the thermistor 60 causes the controller 80 to continue to increase the temperature of heating element 62 until the air reaches the predetermined temperature value.

The expandable member 70 provides tactile feedback to the surgeon regarding the tissue characteristic. In one embodiment, this tissue parameter or characteristic is the pressure exerted by the instrument jaws on tissue. In another embodiment, the tissue parameter or characteristic is the force exerted by the jaws on tissue. With greater tissue thickness, greater pressure is exerted on the tissue, increasing the pressure reading by the sensors which as explained above will cause larger expansion of the expandable member 70 (due to the increased temperature in the chamber 52). The expandable member 70 is illustratively shown on the rearmost portion 21 of the stationary grip 23 of handle assembly 20. In this manner, whether held in the left or the right hand, the user with the thumb can feel the inflatable member to gauge tissue thickness while still maintaining a grip on the handle assembly 20 thus providing the user with the ability to "sense" the tissue. Note that in alternate embodiments, the expandable member can be placed in other regions of the handle assembly, such as the side of the assembly 20.

It should be appreciated that as an alternative to the thermistor described above which measures the temperature to control expansion of the expandable member, other types of measurements can be utilized. For example, the pressure in the air chamber can be measured. The pressure sensor would achieve a dual function as it monitors the air pressure in the chamber 52. As the heating element 62 is heated to increase the air temperature and thus the pressure inside the air chamber 52, the output of the air pressure sensor will change accordingly. The controller continuously monitors the output value of the air pressure sensor. If the pressure measurement of the sensor exceeds a maximum predetermined value, the controller 80 will cut off current flow to the heating element 62, thereby ensuring the system is safe. Further, if the air in chamber 52 does not reach a pressure value corresponding to the output pressure as determined by the tissue data, the measurement of the sensor causes the controller 80 to continue to increase the temperature of heating element 62 until the air in the chamber reaches the predetermined pressure value for desired expansion of the expandable (inflatable) member.

As other alternatives, instead of measuring an air chamber parameter such as temperature or air pressure, an expandable member measurement can be utilized. This can include for example a strain sensor, a displacement sensor or a force sensor (measuring force exerted by the expandable member 70). These sensors can be attached to the expandable member (e.g. balloon). These sensors can be positioned inside or outside the air chamber 52 to monitor the respective parameter of the expandable member 70.

The sensor would achieve a dual function as it monitors the respective characteristic of the expandable member 70. As the heating element 62 is heated to increase the air temperature and thus the pressure inside the air chamber 52, the expandable member 70 will be inflated and the output of the expandable member sensor will change accordingly. The controller continuously monitors the output value of the sensor. If the measurement of the sensor, e.g. the balloon pressure or force exerted by the balloon, exceeds a maximum predetermined value, the controller 80 will cut off current flow to the heating element 62, thereby ensuring the system remains safe. Further, if the expandable member 70 does not reach a pressure (or force) value corresponding to the output value as determined by the tissue data, the measurement of the sensor causes the controller 80 to continue to increase the temperature of heating element 62 until the expandable member 70 reaches the necessary pressure (or force) value for the desired predetermined expansion of the expandable member 70.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a handle portion having a movable handle;
   an elongated body portion extending distally from the handle portion, the elongated body portion defining a longitudinal axis;
   a tool assembly adjacent a distal portion of the elongated body portion, the tool assembly having at least one jaw movable to a clamping position to clamp tissue, the tool assembly actuated by movement of the movable handle;
   a tactile feedback system independent of the movable handle and including an expandable member expandable in response to a change in air pressure, the change in air pressure responsive to a change in a tissue parameter caused by the action of the at least one jaw, the expandable member providing a tactile indicator of the tissue parameter of tissue clamped by the least one jaw; and
   further comprising one or more of: a strain sensor, a displacement sensor, and a force sensor operably coupled with the expandable member.

2. A surgical instrument according to claim 1, wherein the tissue parameter is a force applied by the at least one jaw to the tissue.

3. A surgical instrument according to claim 1, wherein the tissue parameter is a pressure applied by the at least one jaw to the tissue.

4. A surgical instrument according to claim 3, wherein an increase in tissue pressure causes an increase in the air pressure to expand the expandable member and a decrease in tissue pressure causes a decrease in air pressure to decrease expansion of the expandable member.

5. A surgical instrument according to claim 3, wherein an increase in tissue force causes an increase in the air pressure to expand the and a decrease in tissue force causes a decrease in air pressure to decrease expansion of the expandable member.

6. A surgical instrument according to claim 1, further comprising a controller and a sensor positioned adjacent the tool assembly to provide an electrical signal to the controller of the tissue parameter.

7. A surgical instrument according to claim 1, further comprising a controller, the controller positioned in the handle portion external of the air chamber.

8. A surgical instrument according to claim 1, further comprising a thermistor positioned in the instrument to measure the temperature and to provide a cutoff of current if the temperature exceeds a predetermined value.

9. A surgical instrument according to claim 1, further comprising an air chamber, a heating element and a thermistor positioned in the air chamber to measure temperature in the air chamber, the controller terminating current flow to the heating element if a temperature in the air chamber exceeds a maximum temperature value.

10. A surgical instrument according to claim 1, wherein the movable handle is movable relative to a stationary handle of the handle portion, and the expandable member is positioned on a rear surface of the stationary handle.

11. A surgical instrument according to claim 1, further comprising an air pressure sensor positioned in an air chamber of the tactile feedback system and a controller, the controller changing a temperature of a heating element in the air chamber responsive to a measurement of the pressure sensor to correspond to a preset value responsive to a tissue parameter signal sent to the controller.

12. A surgical instrument according to claim 11, further comprising a firing handle to fire fasteners from the instrument, wherein the expandable member is accessible by the thumb of the user while grasping the firing handle of the instrument.

13. A surgical instrument according to claim 1, further comprising an expandable member sensor for measuring a parameter of the expandable member, and further comprising a controller, the controller changing a temperature of a heating element responsive to a measurement of the expandable sensor to correspond to a preset value responsive to a tissue parameter signal sent to the controller.

14. A surgical instrument according to claim 1, wherein the tool assembly supports a plurality of fasteners and the instrument includes a firing mechanism for firing the fasteners from the tool assembly into body tissue.

15. A surgical instrument according to claim 1, wherein the expandable member expands in response to heating of a heating element positioned in the handle portion.

16. A surgical instrument according to claim 15, further comprising a controller and a sensor positioned adjacent the tool assembly to provide an electrical signal to the controller of the tissue parameter, the controller providing an electrical signal to the heating element in response to the tissue parameter.

17. A surgical fastener applying instrument, comprising:
a handle portion including a firing lever; an elongated body portion extending distally from the handle portion, the elongated body portion defining a longitudinal axis;
a tool assembly adjacent a distal portion of the elongated body portion, the tool assembly having at least one jaw movable to a clamping position to clamp tissue and further including a plurality of surgical fasteners;
a sensor positioned adjacent the tool assembly;
a firing mechanism for firing the fasteners from the tool assembly into body tissue upon actuation of the firing handle; and a tactile feedback system responsive to the sensor and including an expandable member extending externally from the handle portion, the expandable member providing a tactile indicator of one of a pressure or force exerted on tissue clamped by the at least one jaw; and further comprising one or more of: a strain sensor, a displacement sensor, and a force sensor operably coupled with the expandable member.

18. A surgical fastener applying instrument according to claim 17, wherein the expandable member expands from a rear surface of the handle portion.

19. A surgical fastener applying instrument according to claim 17, further comprising a thermistor for measuring temperature in the air chamber.

* * * * *